(12) United States Patent
Sena et al.

(10) Patent No.: US 9,521,965 B2
(45) Date of Patent: Dec. 20, 2016

(54) MECHANICAL PIVOT SHIFT MEASUREMENT TO EVALUATE JOINTS

(75) Inventors: Mark Sena, Berkeley, CA (US); Brian Feeley, San Francisco, CA (US); Dezba Coughlin, San Leandro, CA (US); Jeff Lotz, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 765 days.

(21) Appl. No.: 13/570,803

(22) Filed: Aug. 9, 2012

(65) Prior Publication Data

US 2013/0041289 A1    Feb. 14, 2013

Related U.S. Application Data

(60) Provisional application No. 61/521,627, filed on Aug. 9, 2011.

(51) Int. Cl.
*A61B 5/11* (2006.01)
*A61B 5/00* (2006.01)

(52) U.S. Cl.
CPC ............... *A61B 5/11* (2013.01); *A61B 5/1127* (2013.01); *A61B 5/4585* (2013.01); *A61B 5/4884* (2013.01)

(58) Field of Classification Search
CPC ............... A61B 5/11; A61B 2017/0268; A61B 2017/606; A61B 17/60; A61B 17/64; A61B 17/66; A61B 17/7028
USPC .......................................................... 606/57
See application file for complete search history.

(56) References Cited

U.S. PATENT DOCUMENTS

| | | | | |
|---|---|---|---|---|
| 4,306,571 | A * | 12/1981 | McLeod, Jr. | A61B 5/1071 600/595 |
| 7,553,289 | B2 * | 6/2009 | Cadichon | A61F 5/0123 602/23 |
| 2002/0026190 | A1 * | 2/2002 | Walulik et al. | 606/57 |
| 2008/0108918 | A1 * | 5/2008 | Joutras | A61H 1/02 601/34 |

(Continued)

OTHER PUBLICATIONS

Steiner, M.E., "Anatomic Single-Bundle ACL Reconstruction.," Sports Med Arthrosc Rev, Dec. 2009, pp. 247-251, vol. 17, No. 4.

(Continued)

*Primary Examiner* — Adam J Eiseman
*Assistant Examiner* — Yasmeen S Warsi
(74) *Attorney, Agent, or Firm* — Fenwick & West LLP (57) ABSTRACT

An unmet need of orthopedic practitioners is a clinically-relevant measurement device and technique to objectively quantify joint (e.g., knee) stability, including rotational stability. An apparatus and method is disclosed for performing a mechanical joint movement test, such as a knee pivot shift test, through the application of standardized dynamic loads (e.g., using a constant-tension spring or other mechanism). When used for knee evaluation, this test reliably induces the characteristic "pivot" tibial subluxation/reduction event in an ACL-deficient knee, allowing for more sensitive detection of deficiencies in rotational knee stability, quantification of the relative importance of knee stabilizers, and comparison of the performance of contemporary ACL reconstruction techniques. The test allows for better understanding joint biomechanics and for defining unique kinematic and kinetic signatures for common joint injuries, such as knee injuries, that will be valuable for diagnostic purposes.

22 Claims, 7 Drawing Sheets

(56) References Cited

U.S. PATENT DOCUMENTS

2010/0125229 A1* 5/2010 Rudolph .............. A61B 5/1038
602/16

OTHER PUBLICATIONS

Neuman P. et al., "Knee Laxity After Complete Anterior Cruciate Ligament Tear: a Prospective Study Over 15 years," Scand J Med Sci Sports, 2012, pp. 156-163, vol. 22.
Frobell R.B. et al., "A Randomized Trial of Treatment for Acute Anterior Cruciate Ligament Tears," The New England Journal of Medicine, Jul. 22, 2010, pp. 331-342, vol. 363, No. 4.
Oiestad B.E. et al., "The Association Between Radiographic Knee Osteoarthritis and Knee Symptoms, Function and Quality of Life 10-15 Years After Anterior Cruciate Ligament Reconstruction," Br J Sports Med., 2011, pp. 583-588, vol. 45.
Kato Y. et al., "Anatomic Double-Bundle Anterior Cruciate Ligament Reconstruction," Journal of Orthopaedic Science, 2010, pp. 269-276, vol. 15.
Woo S.L. et al., "The Effectiveness of Reconstruction of the Anterior Cruciate Ligament with Hamstrings and Patellar Tendon. A Cadaveric Study Comparing Anterior Tibial and Rotational Loads," The Journal of Bone and Joint Surgery, 2002, pp. 907-914, vol. 84-A.
Tashman S. et al., "Abnormal Rotational Knee Motion During Running After Anterior Cruciate Ligament Reconstruction," The American Journal of Sports Medicine, 2004, pp. 975-983, vol. 32, No. 4.
Shelbourne K.D. et al., "Minimum 10-year Results After Anterior Cruciate Ligament Reconstruction: How the Loss of Normal Knee Motion Compounds Other Factors Related to the Development of Osteoarthritis After Surgery," The American Journal of Sports Medicine, 2009, pp. 471-480, vol. 37.
Louboutin H. et al., "Osteoarthritis in Patients with Anterior Cruciate Ligament Rupture: a Review of Risk Factors," The Knee, 2009, pp. 239-244, vol. 16.
Kocher M.S. et al., "Relationships Between Objective Assessment of Ligament Stability and Subjective Assessment of Symptoms and Function after Anterior Cruciate Ligament Reconstruction," The American Journal of Sports Medicine, 2004, pp. 629-634, vol. 32, No. 3.
Leitze, Z. et al., "Implications of the Pivot Shift in the ACL-Deficient Knee," Clinical Orthopaedics and Related Research, Jul. 2005, pp. 229-236, vol. 436.
Lie D.T. et al., "Persistence of the Mini Pivot Shift After Anatomically Placed Anterior Cruciate Ligament Reconstruction," Clinical Orthopaedics and Related Research, 2007, pp. 203-209, vol. 457.
Markolf K.L. et al., "Relationship Between the Pivot Shift and Lachman Tests: a Cadaver Study," Journal of Bone and Joint Surgery-American, 2010, pp. 2067-2075, vol. 92.
Shoemaker S.C. et al., "Effects of Joint Load on the Stiffness and Laxity of Ligament-Deficient Knees: An in vitro Study of the Anterior Cruciate and Medial Collateral Ligaments," The Journal of Bone and Joint Surgery, 1985, pp. 136-146, vol. 67.
Kanamori A. et al., "The Effect of Axial Tibial Torque on the Function of the Anterior Cruciate Ligament: a Biomechanical Study of a Simulated Pivot Shift Test," Arthroscopy: The Journal of Arthroscopic and Related Surgery, Apr. 2002, pp. 394-398, vol. 18, No. 4.
Snydermackler L. et al., "The Relationship Between Passive Joint Laxity and Functional Outcome After Anterior Cruciate Ligament Injury," The American Journal of Sports Medicine, 1997, pp. 191-195, vol. 25, No. 2.
Harter, R.A. et al., "Long-Term Evaluation of Knee Stability and Function Following Surgical Reconstruction for Anterior Cruciate Ligament Insufficiency," The American Journal of Sports Medicine, Sep./Oct. 1988, pp. 434-443, vol. 16, No. 5.

Pearle, A.D. et al., "Reliability of Navigated Knee Stability Examination: a Cadaveric Evaluation," The American Journal of Sports Medicine, 2007, pp. 1315-1320, vol. 35, No. 8.
Zaffagnini S. et al., "New Intraoperative Protocol for Kinematic Evaluation of ACL Reconstruction: Preliminary Results," Knee Surg Sports Traumatol Arthrosc, 2006, pp. 811-816, vol. 14.
Musahl V. et al., "Mechanized Pivot Shift Test Achieves Greater Accuracy Than Manual Pivot Shift Test," Knee Surg Sports Traumatol Arthrosc, 2009, pp. 1208-1213, vol. 18.
Bedi A. et al., "Transtibial Versus Anteromedial Portal Drilling for Anterior Cruciate Ligament Reconstruction: a Cadaveric Study of Femoral Tunnel Length and Obliquity," Arthroscopy: The Journal of Arthroscopic an Related Surgery, Mar. 2010, pp. 342-350, vol. 26.
Shen W. et al., "Review Article: Anatomic Double Bundle Anterior Cruciate Ligament Reconstruction," Journal of Orthopaedic Surgery, (Hong Kong), 2007, pp. 216-221, vol. 15, No. 2.
Tsai A.G. et al., "Comparative Kinematic Evaluation of Allinside Singlebundle and Double-Bundle Anterior Cruciate Ligament Reconstruction: a Biomechanical Stud," The American Journal of Sports Medicine, 2010, pp. 263-272, vol. 38, No. 2.
Zantop T. et al., "Anterior Cruciate Ligament Anatomy and Function Relating to Anatomical Reconstruction," Knee Surg Sports Traumatol Arthrosc., 2006, pp. 982-992, vol. 14.
Amis A.A. et al., "Functional Anatomy of the Anterior Cruciate Ligament, Fibre Bundle Actions Related to Ligament Replacements and Injuries," The Journal of Bone and Joint Surgery, 1991, pp. 260-267, vol. 72.
Allen C.R. et al., "Importance of the Medial Meniscus in the Anterior Cruciate Ligament-Deficient Knee," Journal of Orthopaedic Research, 2000, pp. 109-115, vol. 18.
Musahl V. et al., "The Effect of Medial Versus Lateral Meniscectomy on the Stability of the Anterior Cruciate Ligament-Deficient Knee," The American Journal of Sports Medicine, 2010, pp. 1591-1597, vol. 38, No. 8.
Lewis P.B. et al., "Systematic Review of Single-Bundle Anterior Cruciate Ligament Reconstruction Outcomes: a Baseline Assessment for Consideration of Double-Bundle Techniques," The American Journal of Sports Medicine, 2008, pp. 2028-236, vol. 36, No. 10.
Carey, J.L. et al., "A Systematic Review of Anterior Cruciate Ligament Reconstruction with Autograft Compared with Allograft," The Journal of Bone & Joint Surgery, Sep. 2009, pp. 2242-2250, vol. 91-A, No. 9.
Wright R.W. at al., "Anterior Cruciate Ligament Revision Reconstruction: Two-Year Results from the MOON Cohort," The Journal of Knee Surgery, Oct. 2007, pp. 308-311, vol. 20, No. 4.
Spindler, K.P. et al., "The Multicenter ACL Revision Study (MARS): a Prospective Longitudinal Cohort to Define Outcomes and Independent Predictors of Outcomes for Revision Anterior Cruciate Ligament Reconstruction," The Journal of Knee Surgery, Oct. 2007, pp. 303-307, vol. 20, No. 4.
Hui C. et al., "Fifteen-Year Outcome of Endoscopic Anterior Cruciate Ligament Reconstruction with Patellar Tendon Autograft for "Isolated" Anterior Cruciate Ligament tear," The American Journal of Sports Medicine, pp. 89-98, vol. 39, No. 1.
Lohmander L.S. et al., "The Long-Term Consequence of Anterior Cruciate Ligament and Meniscus Injuries: Osteoarthritis," The American Journal of Sports Medicine, 2007, pp. 1756-1769. vol. 35, No. 10.
Chaudhari A.M. et al., "Knee Kinematics, cCartilage Morphology, and Osteoarthritis After ACL Injury," Medicine & Science in Sports & Exercise, 2008, pp. 215-222, vol. 40.
Bedi A. et al., "A Comparison of the Effect of Central Anatomical Single-Bundle Anterior Cruciate Ligament Reconstruction and Double-Bundle Anterior Cruciate Ligament Reconstruction on Pivot-Shift Kinematics," The American Journal of Sports Medicine, 2010, pp. 1788-1794, vol. 38, No. 9.
Lane C.G. et al., "The Pivot Shift," Journal of American Academy of Orthopaedic Surgeons, Dec. 2008, pp. 679-688. vol. 16, No. 12.
Bull A.M. et al., "The Pivot-Shift Phenomenon: a Clinical and Biomechanical Perspective," The Knee, 1998, pp. 141-158. vol. 5.

(56) References Cited

OTHER PUBLICATIONS

Kubo S. et al., "Reliability and Usefulness of a New in vivo Measurement System of the Pivot Shift," Clinical Orthopaedics and Related Research, 2007, pp. 54-58, vol. 454.

Musahl V. at al., "The Influence of Bony Morphology on the Magnitude of the Pivot Shift," Knee Surg Sports Traumatol Arthrosc., 2010, pp. 1232-1238, vol. 18.

Musahl V. et al., "Mechanized Pivot Shift Test Achieves Greater Accuracy Than Manual Pivot Shift Test," Knee Surg Sports Traumatol Arthrosc., 2010, pp. 1208-1213. vol. 18.

Pearle A.D. et al., "The Pivot Shift Phenomenon During Computer-Assisted Anterior Cruciate Ligament Reconstruction," The Journal of Bone and Joint Surgery, 2009, pp. 115-118, 91 Suppl 1.

Lopomo N. et al., "Pivot-Shift Test: Analysis and Quantification of Knee Laxity Parameters Using a Navigation System," Journal of Orthopaedic Research, Feb. 2010, pp. 164-169, vol. 28.

Li X. et al., "Cartilage in Anterior Cruciate Ligament-Reconstructed Knees: MR Imaging TI {rho} and T2—Initial, Experience with 1-year Follow-up," Radiology, Feb. 2011, pp. 505-514. vol. 258, No. 2.

Theologis A.A. et al., "Evaluation of Bone Bruises and Associated Cartilage in Anterior Cruciate Ligament-Injured and Reconstructed Knees Using Quantitative $T_{1P}$ Magnetic Resonance Imaging: I-year Cohort Study," Arthroscopy: The Journal of Athroscopic and Related Surgery, Jan. 2011, pp. 65-76, vol. 27, No. 1.

Matsumoto H., "Mechanism of the Pivot Shift," The Journal of Bone and Joint Surgery, Br., 1990, pp. 816-821, vol. 72.

Yamamoto Y. et al., "Effect of the Iliotibial Band on Knee Biomechanics During a Simulated Pivot Shift Test," Journal of Orthopaedic Research, May 2006, pp. 967-973. vol. 24.

Bull, A.M. J. et al., "Incidence and Mechanism of the Pivot Shift. An in vitro Study," Clinical Orthopaedics and Related Research, 1999, pp. 219-231.

Fujie, H. et al., "Forces and Moments in Six-DOF at the Human Knee Joint: Mathematical Description for Control,"Journal of Biomechanics, Dec. 1996, pp. 1577-1585, vol. 29, No. 12.

Forsythe B. et al., "The Location of Femoral and Tibial Tunnels in Anatomic Double-Bundle Anterior Cruciate Ligament Reconstruction Analyzed by Three-Dimensional Computed Tomography Models," The Journal of Bone Joint Surgery, Am., 2010, pp. 1418-1426, vol. 92.

Steckel H. et al., "The Double-Bundle Technique for Anterior Cruciate Ligament Reconstruction: a Systematic Overview," Scand J Med Sci Sports, 2007, pp. 99-108, vol. 17.

Zelle, B.A. et al., "Anatomical Double-Bundle Anterior Cruciate Ligament Reconstruction," Sports Medicine, 2006, pp. 99-108, vol. 36, No. 2.

Kennedy A. et al., "Biomechanical Evaluation of Pediatric Anterior Cruciate Ligament Reconstruction Techniques," Am J Sports Med, 2011, pp. 964-971, vol. 39, No. 5.

* cited by examiner

402 Constant-tension spring
404 External fixation clamps
406 Optotrak markers
408 mounting base

MECHANICAL PIVOT SHIFT MEASUREMENT TO EVALUATE JOINTS

CROSS-REFERENCE TO RELATED APPLICATION

This application claims the benefit of U.S. Provisional Application No. 61/521,627, filed Aug. 9, 2011, which is hereby incorporated by reference in its entirety.

BACKGROUND OF THE INVENTION

Field of the Invention

The invention relates generally to evaluation of joints, and more specifically to mechanical pivot shift measurement to evaluate joints, such as instability in the knee.

Description of the Related Art

The anterior cruciate ligament (ACL) is an intra-articular ligament connecting the lateral femoral condyle to the proximal tibial plateau. The ACL is composed of two distinct functional bundles, the anteromedial (AM) bundle and the posterolateral (PL) bundle. These serve as a primary knee stabilizer and function in concert to limit tibial motion in a manner dependent on the angle of knee flexion. ACL injury is a common occurrence in many sports, with up to 135,000 ACL injuries leading to over 95,000 reconstructions per year in the United States. The ACL is often ruptured in a twisting, non-contact mechanism, with a tear in one of the two bundles occurring 10% of the time, and a complete rupture occurring 90% of the time. In an ACL deficient knee, abnormal kinematics result in medial meniscus tears and degenerative arthritis. The goal of ACL reconstruction is to restore normal knee kinematics, and thereby mechanical/biological homeostasis. Current ACL reconstruction techniques have advanced in the past 20 years to re-establish ACL anatomy, and the immediate outcomes of ACL reconstruction are uniformly good, with 80-95% of patients reporting good to excellent results in many studies. However, despite the short term success of current procedures, the incidence of osteoarthritis is the same in ACL-deficient and ACL-reconstructed knees, indicating that current reconstruction techniques are not adequate in restoring rotational knee kinematics to their native state. Failure to restore rotational stability directly correlates with arthritis progression and poor long-term outcomes.

Given the importance of evaluating rotational stability following ACL-reconstruction, attempts have been made to detect pathological motion patterns in the knee. In a clinical setting, rotational stability of the knee is evaluated with the use of a manual pivot shift maneuver. The pivot shift is a dynamic knee stability test that involves a flexion-dependent combination of an axial force and valgus torque to induce pathologic motion. The presence of a positive pivot shift is predictive of osteoarthritis development, failure to return to previous level of play, patient-reported instability, and poor subjective and objective outcomes following ACL reconstruction.

Despite its correlation with arthritic progression, the pivot shift is highly technique-dependent and variable among practitioners. Consequently, it has poor sensitivity and is difficult to reproduce in a clinical or laboratory setting. Past biomechanical studies have employed various instrumented devices designed to mimic the rotational instability observed in ACL-deficient knees. Since different joint loading combinations induce distinctive kinematic behavior, the results and their interpretation are often inconsistent between studies, making it difficult to determine the effects of graded knee injuries (ligament and meniscus) and different ACL reconstruction techniques, on rotational stability. Thus, improvements in measurement techniques for objectively quantifying knee stability would be valuable to diagnose patients, assess clinical outcomes, and optimize surgical treatment.

SUMMARY OF THE INVENTION

Embodiments provide a method and apparatus for mechanical pivot shift measurement to objectively quantify joint (e.g., knee) stability, including rotational stability. An apparatus and method is disclosed for performing a mechanical joint movement test, such as a knee pivot shift test, through the application of standardized dynamic loads. Among other purposes, when used for knee evaluation, this test reliably induces the characteristic "pivot" tibial subluxation/reduction event in an ACL-deficient knee, allowing for more sensitive detection of deficiencies in rotational knee stability, quantification of the relative importance of knee stabilizers, and comparison of the performance of contemporary ACL reconstruction techniques. The test allows for better understanding joint biomechanics and for defining unique kinematic and kinetic signatures for common joint injuries, such as knee injuries, that will be valuable for diagnostic purposes.

In one aspect, the apparatus and method can measure joint kinematics by applying force to a leg over a range of motion for determining or providing information about a medical condition (e.g., ACL rupture). A force-applying device applies force to the leg to move the leg in a manner that results in a pivot shift test of the knee (e.g., takes the knee through a range of motion and generates a rotation of the tibia relative to the femur). This force-applying device applies a known, predictable, reproducible force and moment profile to the knee joint. One or more sensors can sense the translational and/or rotational position of the tibia and/or femur over this range of motion.

In another aspect, an apparatus for performing a mechanical pivot shift test on the knee includes at least one rigid frame positioned against a portion of the leg for holding the apparatus against the leg and at least one stabilizer attached to the rigid frame for stabilizing an upper or lower portion of the apparatus against a bony portion of the leg. The apparatus also includes at least one fastening strap positioned around the leg and in contact with the frame and the stabilizer for fastening the apparatus to the leg and positioning devices attached to the rigid frame. In addition, the apparatus includes a tension-applying spring attached between the positioning devices, where the positioning devices position the spring in a specific location and orientation with respect to the knee. The spring generates forces and moments about the knee over a range of motion of the knee for performance of the mechanical pivot shift test of the knee.

The features and advantages described in this disclosure and in the following detailed description are not all-inclusive, and particularly, many additional features and advantages will be apparent to one of ordinary skill in the relevant art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

These and other features, aspects, and advantages of the present invention will become better understood with regard to the following description, and accompanying drawings, where.

DETAILED DESCRIPTION OF THE INVENTION

I. Overview

The ACL is one of the most frequently injured stabilizing soft tissue structures within the knee joint. Thus, while the disclosure presented herein can apply to a variety of different joints and/or ligaments associated with joints, the examples here focus primarily on the knee, and particularly on ACL injuries associated with the knee. The method and apparatus are in no way limited by the use of these examples.

Figure 1:
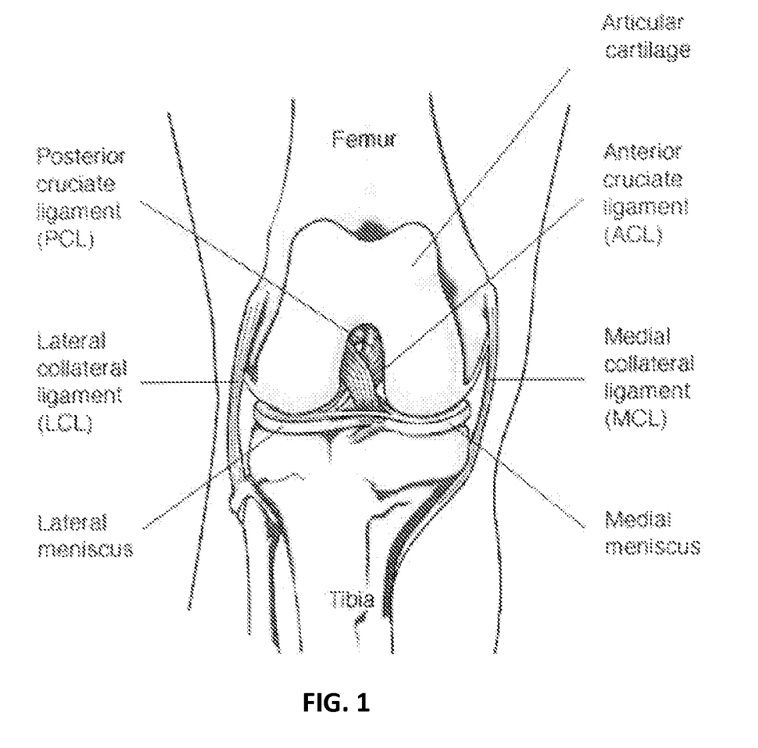
FIG. 1 is a diagram illustrating the knee, including the ACL, according to one or more embodiments.

FIG. 1 is a diagram illustrating the knee, including the ACL, according to one or more embodiments. The ACL is an intraarticular band of dense collagenous tissue. Its function is to limit the combined motions of anterior tibial translation and internal tibial rotation. In addition to the ACL, the medial meniscus (see FIG. 1) has been shown to be an important joint stabilizer, becoming the primary AP restraint in an ACL-deficient knee. One study has evaluated the effect of meniscus injury on rotational instability, finding that the lateral meniscus plays a key role in restraining tibial motion during axial and rotary joint loading. In an ACL deficient knee, abnormal kinematics result in medial meniscus tears and degenerative arthritis.

Following complete rupture, the ACL cannot be repaired, only "reconstructed" using autologous or cadaveric donor tissue. The purpose of ACL reconstruction is to restore normal kinematics to an ACL-deficient knee, particularly anteriorposterior stability and rotational stability (RS). ACL reconstruction involves arthroscopic examination of soft tissue structures and articular surfaces, clearance of damaged tissue, drilling of tibial and femoral tunnels, and placement of an autologous or cadaveric ligament graft. The technique of ACL reconstruction has evolved considerably over the past 20 years, leading to improved clinical results. The KT-1000™ arthrometer is used to measure anterior tibial translation for assessing the success of ACL reconstruction. As a result, surgical techniques that effectively eliminate anterior laxity have become the most prevalent. Objective findings following ACL reconstruction demonstrate a decrease in anterior tibial translation by both clinical examination and instrumented KT-1000™ knee ligament arthrometer evaluation. Recent studies have shown that rotational stability is not always restored after ACL reconstructions employing such techniques, and KT-1000™ measures only anterior-posterior stability, but does not measure rotational stability, which is a more important indicator of outcomes. Some studies suggest that double-bundle reconstruction and single bundle reconstruction with anteromedial portal drilling may improve rotational stability due to more anatomic tunnel placement, but this has not been conclusively determined. Indeed, ACL surgery seems to have become more successful in returning anteroposterior (AP) stability, but it has not been established that the latest techniques restore rotational stability. Thus, despite the introduction of new surgical reconstruction techniques, many patients eventually become dissatisfied with their outcome, often suffering from residual joint pain, loss of mobility, and increased risk of osteoarthritis.

Figure 3:
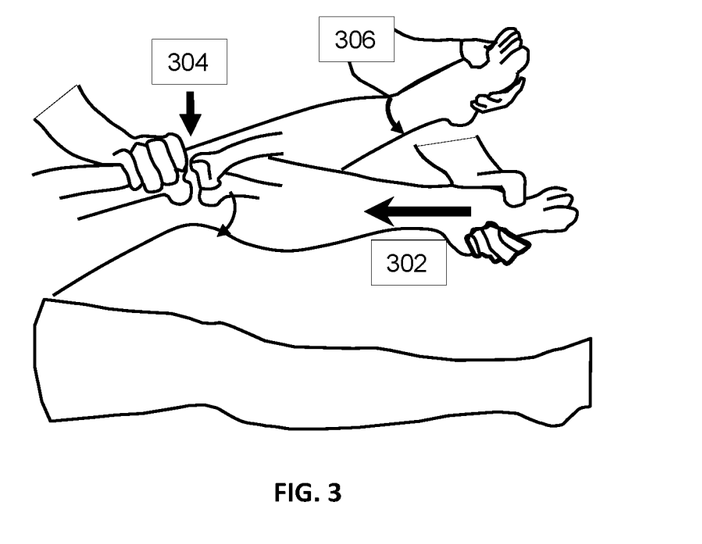
FIG. 3 is a diagram illustrating the manual pivot shift test, according to one or more embodiments.

Currently, AP stability is reliably evaluated using both manual and instrumented exams. Although RS is highly predictive of patient-reported outcome, it is not easily measured in the clinic. The current gold standard is the manual "pivot shift" exam, which is performed by applying an axial load and valgus force to the knee joint, as is illustrated in FIG. 3. In an ACL-deficient state, the pivot shift subluxes (displaces anteriorly and rotates internally) the tibia on the femur in extension; illiotibial band tension then reduces the tibia in flexion. Compared to AP laxity tests, the presence of a positive pivot shift is more predictive of: 1) osteoarthritis risk; 2) failure to return to previous level of play; 3) patient-reported instability; and 4) poor subjective and objective outcome scores following ACL reconstruction. Unfortunately, the manual pivot shift is often difficult to reproduce and interpret, is semi-quantitative (e.g., grade I-III), and exhibits poor specificity, making it hard to standardize exams and accurately compare results between patients and over time. The subjectivity and variability also limits the ability to characterize subtle injury sub-phenotypes and healing progression.

In the laboratory setting, investigators typically impose static loads (e.g., anterior force or internal moment) in order to evaluate joint laxity at discrete flexion angles. However, passive joint laxity is not necessarily correlated with functional stability. Alternatively, researchers may manually manipulate the knee over a continuous flexion motion, with little or no control over the applied forces and moments. The apparatus and methods disclosed here mechanically apply a pivot-shift type test through the application of standardized dynamic loads by a constant-tension spring to reliably induce the pivot shift in an ACL-deficient knee. This allows for more sensitive detection of deficiencies in rotational knee stability, quantification of the relative importance of knee stabilizers, comparison of the performance of contemporary ACL reconstruction techniques, better understanding of knee biomechanics, and definition of unique kinematic signatures for common knee injuries for diagnostic purposes.

Figure 2:
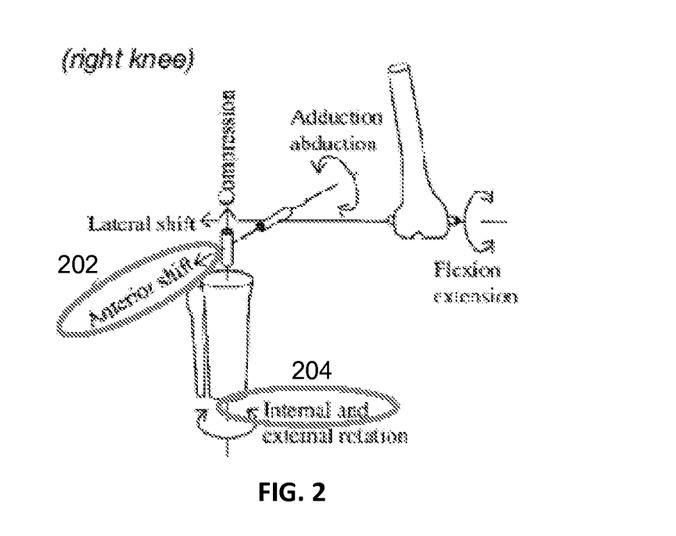
FIG. 2 is a diagram illustrating the anterior translation and internal rotation of the tibia against which the ACL stabilizes the knee, according to one or more embodiments.

FIG. 2 is a diagram illustrating the anterior translation and internal rotation of the tibia against which the ACL stabilizes the knee, according to one or more embodiments. The knee joint has 6 degrees of freedom of motion—3 in rotation and 3 in translation. The knee rotates primarily in flexion/extension, which is coupled to tibial internal/external rotation. The ACL in particular stabilizes the knee against anterior translation 202 and internal rotation 204 of the tibia, as shown in FIG. 2. The combination of joint interface geometry, connective tissue structures, and surrounding muscles ultimately control joint kinematics.

FIG. 3 illustrates the manual pivot shift test, according to one or more embodiments. The pivot shift is a dynamic joint laxity test used to evaluate RS of the knee, and thus ACL integrity. The maneuver involves application of an axial load 302, valgus moment 304, and internal rotation to the tibia 306, as shown in FIG. 3. A positive pivot shift indicative of ACL deficiency involves a sudden tibial reduction associated with a "glide" or "clunk." A positive pivot shift is more predictive than anterior tibial displacement of poor patient outcome. However, the complex combination of multiplanar loads applied during testing is difficult to reproduce in the clinic.

II. Apparatus and Method

The mechanical pivot shift apparatus is an apparatus for measuring joint kinematics by applying force to a leg over a range of motion for determining a medical condition. (e.g., ACL rupture). Various components and designs of the apparatus are described below. These are just some examples of components and designs, though the apparatus could be otherwise designed and could include more, fewer, or different components from those described below.

The apparatus allows repeatable application of specific multiplanar forces and moments to a knee, measurement of the kinematic response of the knee to the applied forces and moments, and evaluation of the mathematical relationships between the loading conditions (forces and moments) and resultant kinematics by calculating and evaluating a stiffness matrix (6×6 matrix relating displacements and rotations to forces and moments (analogous to k=F/x)) for the knee joint. In some embodiments, the mechanical pivot shift test tests for excessive tibial subluxation (anterior displacement and internal rotation of the tibia (excessive if ACL-deficient)), or tibial reduction (posterior displacement and external rotation (indicative of excessive subluxation)) or measures for the characteristic "glide" or "clunk" experienced in a pivot shift test that is associated with an ACL problem. In some embodiments, the apparatus can predict the degradation state of the knee's PL and AL bundle. The mechanical pivot shift apparatus provides a pivot shift test with a higher degree of reproducibility than the manual pivot shift test, and is more standardized and quantitative than the manual test.

The apparatus can include a number of components. In some embodiments, the apparatus includes a force-applying device that applies force to the leg (e.g., to the lower portion of the leg or to the foot) over a range of motion, thereby moving the leg and the knee. The force-applying device or mechanism can take a variety of forms. For example, it can be a tension-applying spring, such as aconstant-tension or constant-force spring that is fixed to the leg or fixed to a device associated with the leg. Other examples include a robotic device that grasps or otherwise moves the leg, a motorized machine that moves the leg, a machine comprising one or more weights, springs, pulleys, and so forth. The force applied can be one or more forces that mimic the forces applied in a manual pivot shift test. For example, the forces can include a valgus, axial, or internal-rotary load during knee flexion or an anteriorly-directed force applied to the tibia. As one example, the force applied can be a measured and controlled force of approximately 50 Newtons axial, 5 Newton-meters valgus, and 5 Newton-meters internal rotation or other values or ranges of values commonly found in pivot shift tests. The apparatus is also designed to apply specified loads continuously, not just at discrete flexion angles.

The apparatus can also include a fixation system or device for fixing the apparatus to the leg at the knee. The fixation system attaches or wraps around the leg in some manner near the knee. However, the design of the fixation system leaves the joint unconstrained by the device. Thus, any wrap or strap near the joint is designed not to interfere with the kinematic response to the applied loads. One example of a fixation system is a knee brace design (e.g., a fabric knee brace with Velcro straps to attach around the leg at the knee). Such a knee brace can be designed to have no hinge at the knee or a very flexible hinge that does not inhibit or interfere with motion of the knee. Another example includes straps that wrap around the leg, such as one strap above the knee and one below. The various components of the device, such as the force applying system, sensors (described below), etc. can be attached or mounted to this fixation system, as desired. In some embodiments, the fixation system also includes at rigid or substantially rigid frame (e.g., an aluminum frame) to which components of the apparatus attach. There can be a single frame or more than one frame or portion of a frame (e.g., one frame for holding the apparatus in place at the shin or tibial region of the leg and one frame for holding the apparatus in place at the thigh or femoral region of the leg). In some embodiments, additional fixation components (pins, rods, clamps, etc.) are attached to the fixation system to mount the force applying device to the fixation system. For example, where the force applying device is a constant force spring, the fixation can have attached to it fixation components for holding the spring in position and possibly away from the leg, with one end of the spring mounted to the portion of the fixation system at the thigh/upper leg and the other end mounted to the portion of the fixation system at the calf/lower leg. In some embodiments, there is no fixation system or a very minimal fixation system, and the system can be attached elsewhere to the body or to other parts of the leg.

The apparatus can also include various sensors. In some embodiments, apparatus includes a sensor that senses the translational and rotational position of a tibia in the leg over range of motion. In some embodiments, the apparatus also includes a sensor that senses the translational and rotational position of a femur in the leg over range of motion. These sensors can be the same or different types of sensors. The sensors can also measure, for example, tibial loads and motion, position, etc. For example, these sensors can take position measurements sufficient to determine the rotational and translational degrees of freedom of the knee over time.

These sensors can take a variety of forms, including any type of optical sensors, mechanical sensors, tension or flexion sensors, infrared sensors, ultrasonic or acoustic sensors, RFID sensors, accelerometer or relative motion sensors, cameras, among others. As one example, the sensors can comprise an optical navigation tracking system, such as an Optotrak system (e.g., Optotrak 3D navigation system).

The apparatus can optionally include a recorder or other mechanism that records the positions sensed by the sensors. For example, the recorder can record a sensed first and second position of the leg or knee (or of the tibia and femur, or tibia and femur relative to each other). The recorder can also record the force applied by the force-applying device, and the resistance over the range of motion. In some embodiments, the recording is sufficient to allow determination of the translational and rotational position of the knee over the range of motion during the pivot shift test. In some embodiments, the recording performed is a recording of a stiffness matrix relating displacements and rotations of the knee to forces and moments over a time period. In other embodiments, the apparatus does not include a recorder, since it is possible to specify the forces/moments applied to the joint without necessarily recording them.

The recording system and/or the sensors can be or form a part of a motion capturing system used with the mechanical pivot shift apparatus. In some embodiments, the motion capturing system includes one or more cameras used for detecting the sensor or marker positions on the body. A variety of different motion capturing systems can be used, including single-, dual-, or three-camera systems (or additional cameras, as needed). In some motion capture systems, multiple cameras are encased into one piece of equipment (e.g., Optotrak systems). In other systems, there can be different and separate cameras that are positioned at specific locations around a room. These cameras can take pictures of the joints during motion, including the markers or sensors positioned on the body. The markers/sensors can provide some sort of signal that can be captured by the camera. The markers/sensors can be active markers providing an active signal, or passive markers that passively provide the signal. An example of an active marker is an infrared strobing marker (e.g., active strobing infrared LED), where the camera captures the infrared strobing of the markers positioned at various locations on the body for recording the joint positions and movement. An example of a passive marker is a reflector (e.g., a passive infrared reflector), where the camera captures the positions of the passive markers at various locations on the body.

The apparatus can also include a pre-determined signature that can assay the recording taken by the recorder to determine if a medical condition is indicated by the recorded positions, forces, and resistances over the range of motion. For example, the signature can be a kinematic signature indicative of a particular knee defect, such as a ruptured ACL. The signature can also be a signature to assay the rotational stability of the knee or a signature to assay the medical condition of the ACL, the degree of tearing of the ACL, the anterior-posterior stability of the knee, etc. The signature can further include trajectories of tibial translations and rotations over a range of flexion of the knee. As another example, the signature can include measurements of the maximum internal tibial rotation, maximum anterior displacement, posterior tibial velocity, initial internal rotation, initial anterior displacement, lateral compartment displacement, medial compartment displacement, among other parameters.

The apparatus can also include a prediction program that predicts particular problems with a joint, such as a deficiency in the specific structures of the knee (e.g., predicts the type and degree of damage to the ACL bundles and medial/lateral meniscus). In some embodiments, this program can calculate a knee stability index and report the index to a user.

The apparatus can operate in various manners. In one embodiment, the force-applying mechanism applies a force to the lower leg and moves the lower and upper leg through a range of motion that includes rotating the lower leg and bending the knee, and the sensors sense the positions and force. A signature-evaluator or other mechanism can apply the signature to the information recorded by the recorder, and can thereby make a determination of whether a particular medical condition is met (e.g., whether the ACL has been ruptured).

Figure 4A:
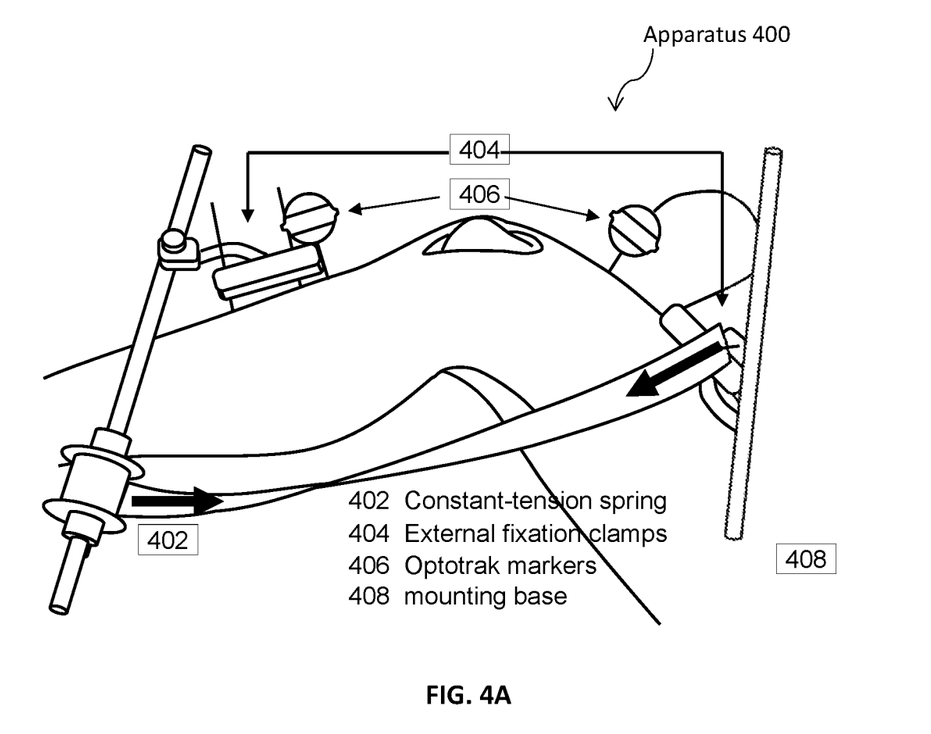
FIG. 4A is a photograph of an experimental mechanical pivot shift apparatus, according to one or more embodiments.

FIG. 4A is a photograph of an experimental mechanical pivot shift apparatus 400, according to one or more embodiments. This is just one example of such an experimental apparatus, though a variety of other designs are also possible, including any of the components described above regarding the apparatus. The apparatus 400 of FIG. 4 includes a number of components, including a constant-tension spring 402, external fixation device (e.g., clamps) 404, markers (e.g., Optotrak markers) 406, and a mounting base or other mechanism for mounting the components 408. The apparatus may include more or fewer components, depending on the design. During knee flexion, a tensile force (red arrows) is applied between the ends of a constant-tension spring 402. For example, the force can be a 48N tensile force. An external fixation kit 404 is used to position the spring in the desired configuration. Markers, such as Optotrak markers, allow for measurement of pivot kinematics. The constant-tension spring 402 can apply a single known force between the tibia and femur. As the knee is flexed, the spring 402 orientation changes and the components of the resultant force/moment vectors vary in a way that simulates a manual pivot shift test. Since this is an experimental model of the mechanical pivot shift apparatus, it is fixed to the leg using an external fixation system 404 that involves rods and clamps, with pins actually entering the leg. However, in clinical, non-experimental user, a patient-friendly fixation system would be used, such as a knee brace design (as described above) to which the spring or other force-applying mechanism could be attached along with the sensors or Optotrak markers. Multivariate statistical analysis can be performed to identify kinematic "signatures" of specific knee defects. This analysis uses quantified metrics that capture important features of the complex motion measured during the pivot shift test and can be used to develop a diagnostic test with improved clinical value (e.g., a "knee stability index").

The apparatus 400 can be used to evaluate the effects of 1) graded joint defects, and 2) different common ACL reconstruction techniques, on rotational knee stability. In addition, the apparatus 400 can be used in developing a robust, non invasive, clinical diagnostic test that is sensitive and specific to graded defects of the main knee stabilizers: the collateral and cruciate ligaments and medial/lateral meniscus. This provides a more accurate method of clinically evaluating rotational stability before and after different ACL reconstruction techniques. This will also lead to a lower incidence of disabling arthritis following ACL reconstruction by better matching treatment modalities to injury sub-phenotypes. The apparatus 400 can also be used to link robust measures of knee biomechanics to sensitive indices of early cartilage degeneration quantified in vivo by MRI.

Figure 4B:
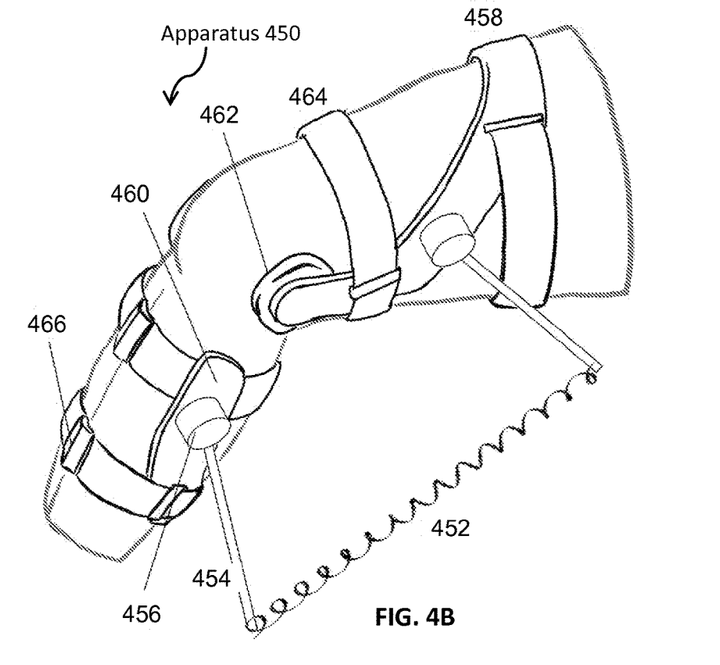
FIG. 4B is a diagram of the clinical mechanical pivot shift apparatus, according to one or more embodiments.

FIG. 4B is a diagram of the clinical mechanical pivot shift apparatus 450, according to one or more embodiments. This is one example of a design that could be used for clinical or in vivo usage of the device, though other designs can include more, fewer, or different components than those shown in FIG. 4B. The apparatus includes a tension-applying spring 452, spring positioning rods 454, rod-positioning hubs 456, a femoral rigid frame 458, a tibial rigid frame 460, femoral epicondyle stabilizers 462, tibial ridge stabilizers 464, and fastening straps 466. The tension-applying spring 452 is the component that generates the pivot shift forces and moments about the knee joint. As explained above, this is one embodiment of a force applying device. In some embodiments, this tension-applying spring 452 is a constant-tension spring or a standard linear spring where the spring constant is known. The spring-positioning rods 454 are lightweight rigid rods used to position the spring 452 in a specific location and orientation (e.g., 6-degrees of freedom, total) with respect to the knee joint. Spring positioning determines the force/moment profile generated during knee flexion. The rod-positioning hubs 456 are rotating hubs that can have several preset configurations (e.g., presets calibrated for different patient heights) for the rod position, though these can also be freely-swiveling hubs, without presets. The rods 454 and hubs 456 are examples of the fixation components described above that are used to fix the force applying device (in this case, spring 452) to the apparatus or fixation system.

The femoral rigid frame 458 holds the upper half of the apparatus against the patient's thigh or upper leg (e.g., in the region of the femur), while the tibial rigid frame 460 holds the lower half of the apparatus against the patient's shin or lower leg (e.g., in the region of the tibia). These are examples of the rigid frame described above that can form a part of the fixation system. Femoral epicondyle stabilizers 462 stabilize the upper half of the device on the bony femoral epicondyles and tibial ridge stabilizers 464 stabilize the lower half of the device on the bony tibial ridge. Fastening straps 466 hold the rigid frames and stabilizers firmly against the patient's leg. The stabilizers 462, 464, and straps 466 all can form a part of the fixation system described above for fixing the apparatus to the leg. In some embodiments, the tibial and femoral halves of the apparatus 450 are designed to be independent of each other, and designed so that neither interferes with the motion of the knee. In this manner, the primary or only factors influencing knee motion are the spring, which can be controlled in the apparatus 450 and the knee itself, the joint being measured by the apparatus 450. The apparatus 450 operates in generally the same manner as described above for apparatus 400 and can be used to evaluate the same effects described for apparatus 400.

III. Experimental Examples

A. Preliminary Studies.
1. Manual Pivot Shift Test Versus Mechanical Pivot Shift Apparatus.

The mechanical pivot shift apparatus was used to reproduce a positive pivot shift in an ACL-deficient cadaver knee. The apparatus applied a standardized combination of multiplanar forces and moments to the knee utilizing a constant-tension spring, as illustrated in FIG. 4 to induce a consistent tibial subluxation/reduction event during knee flexion. The mechanical pivot shift apparatus was used to compare the 3D rotational and translational kinematics of knee motion during manual and mechanized pivot shift tests. Each test type was performed 3 to 5 times on both intact and ACL-deficient cadaveric knees (3 knees).

Figure 5:
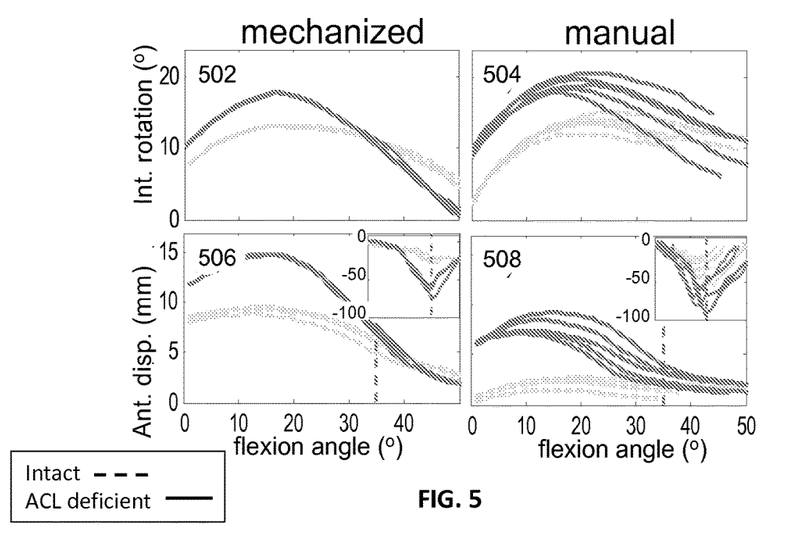
FIG. 5 is a graphical illustration of typical pivot shift trajectories for the manual pivot shift test performed manually and for the mechanical pivot shift test performed with the mechanical pivot shift apparatus, according to one or more embodiments.

FIG. 5 is a graphical illustration of typical pivot shift trajectories for the manual pivot shift test performed manually and for the mechanical pivot shift test performed with the mechanical pivot shift apparatus, according to one or more embodiments. The graphs show movement of the tibia relative to the femur during a manual test and using a mechanical pivot shift apparatus, including the anterior displacement and internal rotation. In ACL-deficient knees, the mechanical pivot shift apparatus was successful in mimicking the internal rotation and anterior translation trajectories of a manual pivot shift maneuver performed by an experienced clinician, as is shown in FIG. 5. The graphs show that the curve for the mechanized test was qualitatively similar to the manual test, however the lines of the curve for the mechanical test were much more tightly spaced, indicating the higher reproducibility of the mechanical test.

Under the influence of the forces and moments generated by the apparatus, the tibia first became subluxed at a knee flexion angle of 17±1°. At an angle of 35±2°, the tibia was then rapidly reduced, exhibiting peak posterior velocities (PPV) near 70 mm/s Intact knees became only slightly subluxed, and did not exhibit rapid tibial reduction. Addition of a 44 N force applied to the illiotibial (IT) band did not result in an increased pivot, suggesting that this aspect was not necessary in order for the apparatus to produce a realistic pivot. The apparatus was significantly more precise in comparison to the manual maneuver between multiple tests performed on the same knee. For example, the maximum standard deviation of the maximum tibial IR ($IR_{max}$) was 0.85° (n=3) for the device, as compared to between 3.2° and 7.2° for two practitioners. When comparing matched right and left knees using the device, $IR_{max}$ and maximum anterior displacement ($AD_{max}$) differed by less than 1.5° and 2 mm in either the intact or ACL-deficient state. These results demonstrate the capacity of apparatus 400 to produce a realistic pivot shift in an unstable knee with a high degree of reproducibility. FIG. 5 illustrates that the intact and ACL-deficient pivot shift trajectories were more reproducible using the apparatus (n=3, left) than by manual maneuver (n=5, right). For both test types, internal rotation (IR, top), anterior displacement (AD, bottom), and posterior tibial velocity (PTV, inset) followed similar courses relative to knee flexion angle. A pivot occurred at ~35°.

2. Comparison of ACL-Intact Versus ACL-Deficient States.

Figure 6:
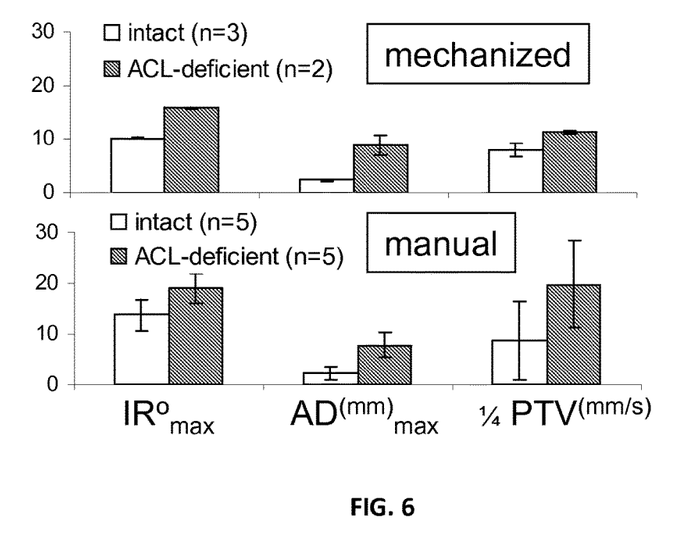
FIG. 6 is a graphical illustration of quantitative pivot metrics for the manual pivot shift test performed manually and for the mechanical pivot shift test performed with the mechanical pivot shift apparatus, according to one or more embodiments.

Using the mechanical pivot shift apparatus, the kinematic differences between intact and ACL-deficient knee states was measured with less variability relative to a manual test. Both test types were performed in series on a knee in the intact and ACL-deficient states. The manual and mechanical tests demonstrated increased $IR_{max}$, $AD_{max}$, and PTV, as shown in FIG. 6. However, the coefficient of variation (cv=σ/ν was significantly less in the metrics of the apparatus (mean cv=0.028) in comparison to the manual metrics (mean cv=0.16). Thus, the apparatus reproducibly performed a clinically relevant and precise pivot of the ACL intact and deficient state.

FIG. 6 is a graphical illustration of quantitative pivot metrics for the manual pivot shift test and for the mechanical pivot shift test performed with the mechanical pivot shift apparatus, according to one or more embodiments. FIG. 6 shows that the $IR_{max}$, $AD_{max}$, and PTV values from apparatus tests (top) had tighter 99% CIs than values from manual maneuvers (bottom). For both test types, metric values were smaller in magnitude for intact relative to ACL-deficient knee states. The height of the bars in the graph represent the height of the peaks in the curves of FIG. 5.

Figure 7A:
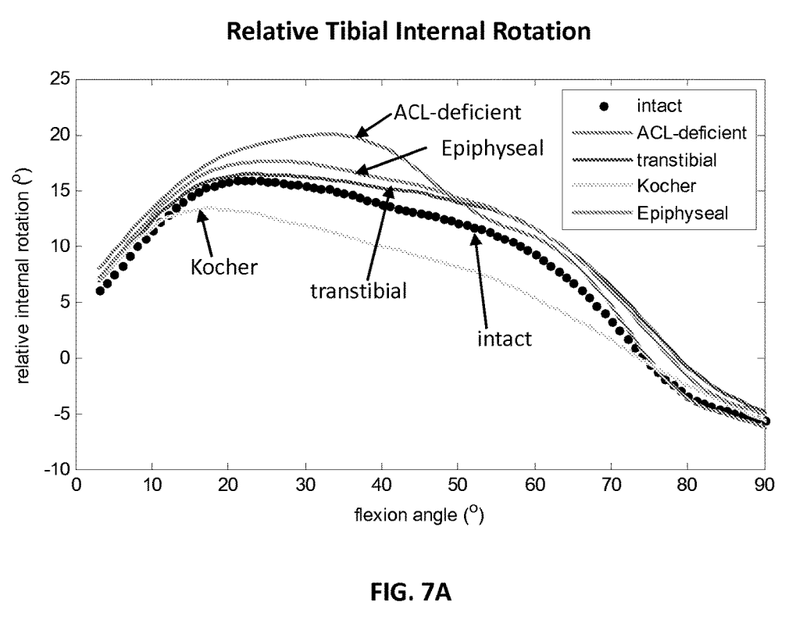
FIG. 7A is a graphical illustration of internal rotation (degrees) during a mechanical pivot shift test, according to one or more embodiments.
Figure 7B:
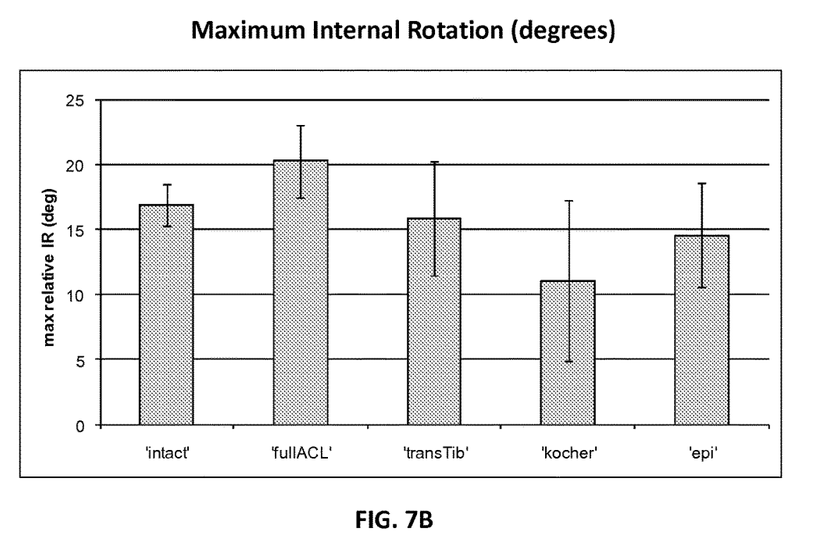
FIG. 7B is a graphical illustration of the maximum value of internal rotation, according to one or more embodiments.

FIG. 7A is a graphical illustration of internal rotation (degrees) during a mechanical pivot shift test, according to one or more embodiments. FIG. 7B is a graphical illustration of the maximum value of internal rotation, according to one or more embodiments. These figures illustrate the relative internal tibial rotation and maximum internal rotation for a knee with an intact ACL, for an ACL-deficient knee, and for 3 different knee reconstruction techniques. As used in FIG. 7A and FIG. 8A, "relative" means rotation and displacement of (a) the tibia in the loaded condition (with the mechanical pivot shift apparatus attached) relative to (b) the rotation and displacement of the tibia in the unloaded condition (nothing attached—just gently lowering the tibia). Data for (a) and (b) were aligned so that the knee flexion angles match (e.g., 1 data point per degree of flexion on the horizontal axes)

Figure 8A:
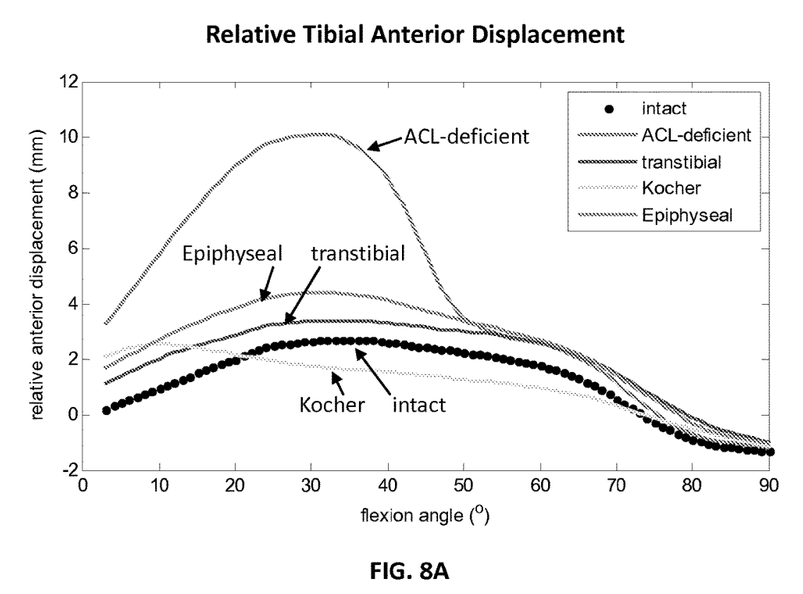
FIG. 8A is a graphical illustration of anterior displacement (mm) during a mechanical pivot shift test, according to one or more embodiments.
Figure 8B:
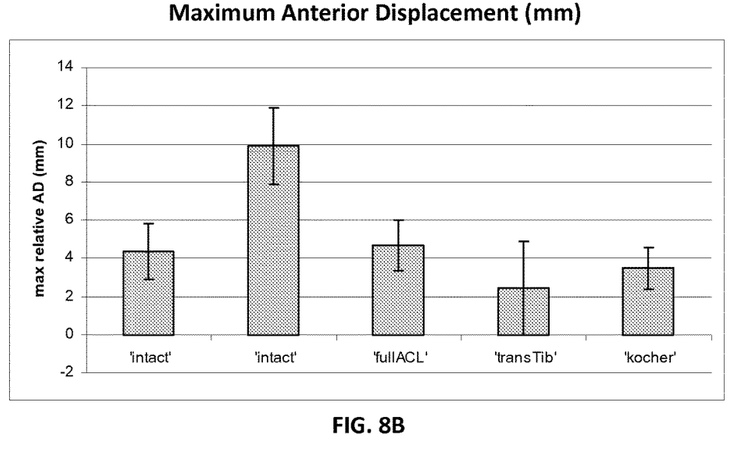
FIG. 8B is a graphical illustration of maximum value of anterior displacement, according to one or more embodiments.

FIG. 8A is a graphical illustration of anterior displacement (mm) during a mechanical pivot shift test, according to one or more embodiments. FIG. 8B is a graphical illustration of maximum value of anterior displacement, according to one or more embodiments. These figures illustrate the relative anterior displacement and maximum anterior displacement for a knee with an intact ACL, for an ACL-deficient knee, and for 3 different knee reconstruction techniques.

3. Multivariate Analysis to Predict Knee State.

Logistic regression procedures (JMP; version 7.0) were used to relate the categorical knee state (intact, partial ACL deficient, ACL deficient) to continuous measurements made during the pivot shift test ($IR_{max}$, $AD_{max}$, PTV; n=5 tests each from 3 knees). Univariate analysis demonstrated that $IR_{max}$ was best predictive of ACL condition and explained 40% of the variance (R2=0.41, p=0.0001). The knee state (ACL intact, ACL AM bundle transection, ACL PL bundle transection, ACL complete) was predicted with complete accuracy when the logistic regression included two variables, $IR_{max}$ and PTV ($R^2=1$, p=0.0001). These data suggest that measurements made using the mechanical pivot shift apparatus are sensitive to ACL condition and provide valuable clinical information.

4. Force/Moments during Pivot Shift.

Based on a constant spring tension of 48N and the recorded position of the spring relative to the tibia, the loads applied to the knee joint by the mechanical pivot shift apparatus were estimated over the course of knee flexion. With the knee held at full extension, ~48N axial compression and ~8N.m valgus torque were initially applied. Such loads are consistent with those applied by a clinician to sublux the tibia. As the knee is taken through flexion, apparatus-induced axial/valgus loads decrease while a posteriorly-directed force and external torque increase. Posterior/external loading is consistent with the behavior of the IT band, which is largely responsible for reduction of the tibia during a manual pivot.

The calculations predict that: 1) the mechanical loads produced by the apparatus are similar to those manually imposed by a clinician in subluxing an ACL-deficient knee; and 2) loading patterns vary during flexion and mimic the behavior of the IT band in dynamically reducing the tibia. Using the data acquisition techniques described below, a larger sample size will be used to validate the force/moment estimates and preliminary kinematic results, and test the hypothesis that the sensitivity of the apparatus is higher than the current manual test.

Figure 9:
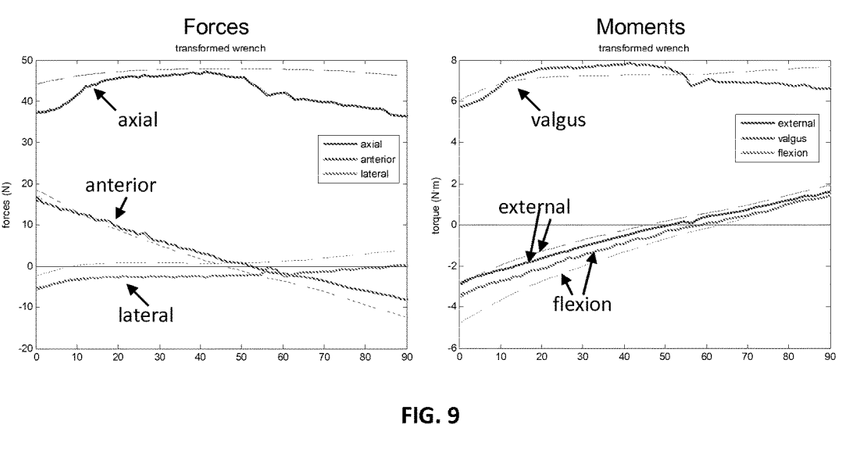
FIGS. 9, 10, 11, and 12 are graphical illustrations of forces and moments associated with usage of the apparatus 400, according to one or more embodiments.
Figure 10:
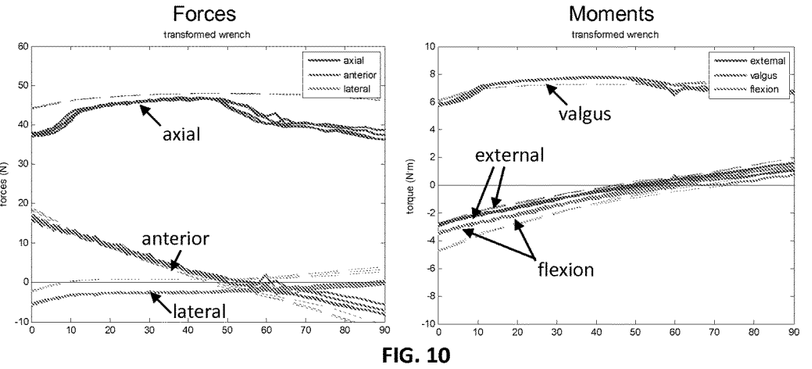
Figure 11:
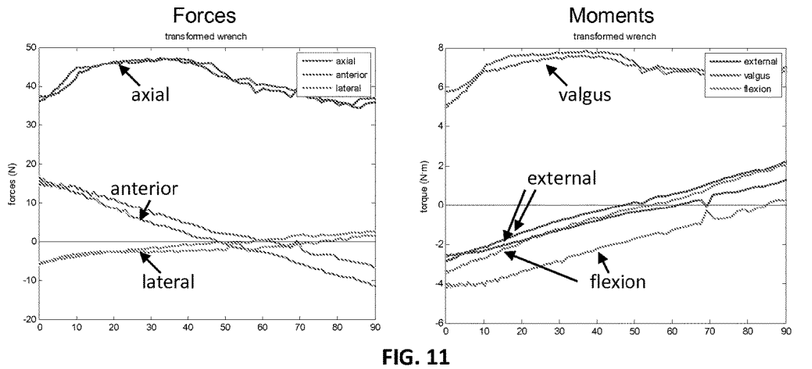
Figure 12:
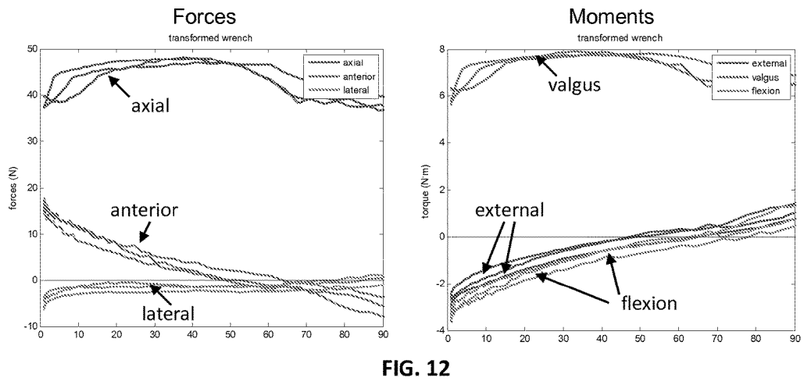

FIGS. 9, 10, 11, and 12 are graphical illustrations of forces and moments associated with usage of the mechanical pivot shift apparatus, according to one or more embodiments. The dotted lines show the calculated loads on the apparatus based on measured kinematics and assumed spring force. The solid lines show the actual loads measured using the load cell that is inserted in the apparatus 400 for determining whether the predictions were accurate. To get the lines as shown in the graph, the spring of apparatus 400 was carefully and reproducibly positioned in the apparatus 400. FIG. 9 illustrates that the forces and moments can be predicted and/or designed. FIG. 10 presents the results of four repeat tests performed on a single knee, and so illustrates that the forces and moments are reproducible for a single knee. The dashed lines of FIGS. 9 and 10 illustrate loading pattern estimates for the mechanical pivot shift apparatus. The apparatus loading follows the trend expected during a manual test. Valgus and external moments (left axis) and combined axial and posterior forces (right axis) were calculated based on recorded kinematics, registered constant-tension spring positions, and a spring force of 48N. FIG. 11 presents the results of tests performed on different knees, and so illustrates that forces and moments are similar for different knees. There was less than 5 N and 2 Nm variability in forces and moments between different knees used. FIG. 12 presents the results of tests performed on a single knee, and illustrates that forces and moments are similar for different knee states. There was less than 10 N and 2 Nm variability in forces and moments between different states of the same knee (e.g., fully intact knee, ACL-deficient, etc.).

The above-described experimental uses allowed for (1) evaluation of a novel mechanized pivot shift device and (2) testing of a unique analysis method for quantitative assessment of rotational knee stability under controlled laboratory conditions. The experimental design provides: 1) a testing apparatus for the reproducible application of dynamic forces and moments to the knee during a simulated pivot shift test, and 2) an integrated data acquisition system for accurate measurement of manual/mechanized loads and the resultant 3D tibio-femoral motion. This allows for control of the magnitude and direction of loads applied to the tibia, evaluation of their effect on pivot shift kinematics in different knee states, and if necessary, alteration mechanized loading to better match a clinical pivot.

B. Comparison of Novel Mechanical Pivot and Standard Manual Pivot.

1. Specimen Preparation and Data Acquisition.

The mechanical pivot shift apparatus 400 of FIG. 4 will be used for these experiments. Fresh-frozen full lower limb specimens will be sectioned and potted using Smooth-Cast. The cylindrical pot will then be bolted to a hinged testing base, containing a 6-axis force/moment sensor (load cell). The hinge allows the specimen to rotate freely at the base about an axis parallel to the flexion-extension axis of the knee. This single degree of freedom permits the examiner to perform a realistic (i.e., with the hip flexing passively along with the knee) manual pivot shift maneuver. The moment about this axis is identically zero, thus flexion and extension of the knee and base hinge do not contribute to load cell measurements. During mechanized tests the hinge is fixed and the femur remains stationary. To replicate iliotibial (IT) band tension, a 4.5 kg weight is suspended from cord sutured to the isolated IT band. In agreement with other reports, it was noted that this was necessary to generate a positive manual pivot shift, but the test using apparatus 400 could reliably be conducted with or without this weight. Kinematic trajectories will be recorded using an Optotrak navigation system, though other systems could be used. The Optotrak 3D navigation system used includes a 3-aperture position sensor (accuracy 0.1 mm and 0.1°), 2 infrared strobing markers attached to the tibia and femur, and a handheld digital probe for registration of reference points. This system has been previously validated and used in biomechanical studies. Femur and tibia origins are defined at the intercondylar notch and center of the tibial plateau; X-axes coincide with the longitudinal bone axes; and points on the medial epicondylar eminence and the proximal tibial ridge define the XZ and XY planes, respectively. The points at which the constant-tension spring attaches to the tibial and femoral rods are registered to ensure consistent spring placement.

2. Application of Pivot Shift Apparatus.

To facilitate proper positioning of the constant-tension spring, a series of clamps and rods are attached separately to the lateral side of the tibia and femur using a surgical external fixation system. Pin clamps with outrigger posts are rigidly secured to the bone using Schanz screws, as illustrated in FIG. 4. Carbon fiber rods are then mounted using small swivel clamps, which allow the rods to be positioned freely in space. Finally, the constant tension spring is attached to the tibial and femoral rods. Before performing an experiment, the 3D coordinates of the spring attachment points between the rods are digitally registered using the Optotrak navigation system. This step allows positioning of the spring attachments within 5 mm of a chosen location relative to the tibia and femur, and allows accurate quantification of the applied forces and moments during the test. Precise placement of the spring ensures that the same forces and moments are applied between tests.

3. Manual versus Apparatus Pivot in Intact and ACL-Deficient States.

A total of 10 knees will be used for this study. After the knees have been set up as described in above, a manual pivot test will be performed in triplicate by two experienced knee surgeons who specialize in arthroscopic ACL reconstruction. The surgeons will be instructed to perform the pivot shift exam as they would in a clinical situation in an ACL-intact state. Given the potential effect of the IT band on the ability to perform an accurate manual pivot 47, a 44-N force will be applied in line with the femur by attaching a weight to the IT band proximally. Next, the constant-tension spring will be applied and three mechanical pivots will be performed in an ACL-intact state (without the IT band force), repeated in triplicate. After ACL-intact data is collected, a small anterior arthrotomy will be made and knees will undergo ACL transection. Rotational stability will be compared in the manual vs. apparatus 400 states.

4. Force/Moment Evaluation.

As the knee is taken through its range of motion, forces and moments will be calculated using a 6-axis load cell to measure the forces and moment vectors at the testing base, and transforming them to the knee joint coordinate system as described by Fujie et al. The resultant forces and moments are calculated given the 3D coordinates of the spring attachment points relative to the tibia. For the manual test, the load cell will be placed at the mounting base and for the apparatus 400, at the tibia.

5. Data Analysis and Outcomes.

As the knee is taken through a range of flexion, θ, joint configuration is represented as a set of tibial translations $T(\theta(t))=[T_x, T_y, T_z]$ and rotations $R(\theta(t)=[R\psi, R\phi]$ of the tibia relative to a full-extension reference configuration $(R(0), T(0))$. The data will be recorded using the Optotrak 3D position tracking system and the data processed using MATLAB Software. The primary variables obtained will be maximum internal tibial rotation (IRmax), maximum anterior displacement ($AD_{max}$), and posterior tibial velocity (PTV). Secondary variables of interest include initial internal rotation, initial anterior displacement, lateral compartment displacement, and medial compartment displacement.

6. Statistical and Power Analysis.

Standard analysis of variance procedures will be used to calculate group means and to determine significant differences in the primary measured parameters of interest—IRmax, ADmax, and PTV—as a function of ACL status. Inter- and intraobserver reliability will be compared with an interclass correlation in the manual and MPSD groups to determine the precision of the manual compared MPSD. As a measure of reproducibility, the coefficient of variability will be calculated for each measurement (standard deviation divided by the mean).

For planning purposes, a 95% confidence interval was assumed around sensitivity and specificity (assuming a normal approximation to a binomial distribution) in order to predict the desired sample size. The experiments target an AUC of 0.95 with a precision of ±0.05, and will probably require 10 knees.

7. Expected Results.

It is anticipated that the apparatus 400 will be more reproducible within each knee as well as between knees when compared to the manual pivot shift when evaluating inter- and intra-observer reliability. In addition, it is predicted that there is considerable variability between experienced knee surgeons in the force/moment data obtained in the manual pivot experiment. Based on the preliminary studies, it is predicted that the apparatus 400 will be able to distinguish between intact and complete ACL deficiencies and will have significantly better reproducibility as defined by the coefficient of variability.

The force/moment combinations required to produce a pivot shift may need to be individualized on a knee to knee basis. However, this applied only to static tests and required IT band force. Since the apparatus 400 provides a dynamic test that does not require an IT band force, the same loading conditions can be applied to multiple specimens. By choosing different spring positions and strengths, multiple standardized loading profiles can be applied to each knee. This will allow testing of whether individual force/moment combinations are actually necessary for each knee. The experimental design can account for variation in apparatus 400 test speed by normalizing PTV by the recorded flexion velocity.

C. Comparison of Graded Knee Deficiencies.

The purpose of this experiment is to quantify and rank the biomechanical consequences of graded defects of the main anterior and rotational knee stabilizers: the ACL and the medial/lateral meniscus. With the mechanical pivot shift apparatus, it should be possible to detect the effects of partial and complete ACL deficiency (both AM and PL bundles) on rotational kinematics of the knee, as well the effects of medial/lateral meniscus tears on rotational kinematics. The results of the Aim 2 studies will be to establish the coefficients for a logistic regression model that will take apparatus measurements as inputs and provide the clinician the percent probability that a given knee has a disruption of either the ACL bundles or menisci. This probability number will characterize overall "knee stability index" and indicate which structures are deficient.

1. Evaluation of Graded Knee Deficiencies.

After the knees have been mounted as described above, the apparatus 400 test will be performed on the ACL-intact state in triplicate on each knee. This will be repeated in the partial ACL deficiency (AM-6 knees; PL-6 knees) and complete ACL deficiency. Knees will then undergo a partial (50% resection) medial or lateral meniscus tear (six knees in each group) followed by a complete tear, compatible to a radial tear or posterior root tear. To control for the effects of the ACL and meniscus, six knees will undergo an isolated partial and complete medial meniscus tear, and another six, an isolated partial and complete lateral meniscus tear.

2. Data and Power Analysis.

Kinematic data will be collected and reported as described above. Comparisons will be made between each group and statistical analysis will be performed as described in section D.2.7. The primary outcomes will be $IR_{max}$, $AD_{max}$, and PTV and also included in a logistic regression model that relates the continuous parameters to the categorical ACL-status variable (intact, partial, disrupted). A p-value<0.05 will be considered to be statistically significant, while the coefficient of determination ($R^2$) will be used to quantify the percent of variation in the categorical classification that was explained by the logistic model. This will be used to categorize the overall knee stability. The performance of this diagnostic algorithm will also be assessed using Receiver Operating Characteristics (ROC) curves that plot sensitivity versus specificity. The summary of the algorithm's goodness-of-fit will be quantified by the area under the ROC curve (AUC; 0.5 means no predictive value and 1.0 means a perfect fit). During the ROC analysis, JMP also calculates the percent-probability that a given sample is correctly classified. The percent probability that a sample is classified as having an ACL deficiency and meniscus injury will be used to define the knee stability index.

A 95% confidence interval was assumed around sensitivity and specificity in order to predict the desired sample size. An AUC of 0.95 was targeted, with a precision of ±0.05, and six knees will probably be tested in each configuration, for a total of 24 knees.

3. Expected Results.

The graded defects of the knee will probably result in increased rotational instability as measured by the primary variables as well as with the linear regression model, with the PL bundle resulting in a greater increase in rotational instability compared to the effects of the AM bundle. In addition, medial meniscus deficiency will result in a greater increase in rotational instability than the lateral meniscus, but that it will be significantly greater than the intact state overall due to the role of the posterior horn medial meniscus in knee stability 26. Kinematic signatures should be identified that are unique for each surgically-induced defect. This will be demonstrated by a successful logistic regression model (R2>0.8; p<0.05).

Bony morphology, native ligament laxity, and damage to other soft tissue structures have been known to alter pivot shift kinematics. Thus, knee to knee variability may mask absolute changes in pivot shift metrics. Since this is an in vitro cadaver study, it is possible to investigate the effects of graded knee stabilizer defects on an individual basis. As the intra-specimen variability for the mechanical pivot shift apparatus is extremely low, subtle differences in kinematic metrics can be accurately measured relative to the intact state and thus can be normalized between groups if there is significant intra-specimen variability. It is also possible that there will be no significant difference in the graded knee defects noted in the primary variables when comparing the different reconstruction techniques. If this occurs, the secondary variables described in Section B.5 can be evaluated.

D. Comparison of Three Different ACL reconstruction techniques.

The goal of this experiment is to evaluate the rotational stability of three different ACL reconstruction techniques: traditional single bundle trans-tibial (TT) reconstruction, single bundle with anteromedial portal femoral tunnel drilling (AM), and double-bundle (DB) reconstruction. It is hypothesized that more anatomic reconstructions (AM reconstruction and DB reconstruction) result in improved rotational stability compared to the traditional TT technique as defined by $IR_{max}$, $AD_{max}$ and PTV. By using the knee stability index as described in Section B, it is hypothesized that the AM and DB reconstructions will approach the knee stability index of the intact knee.

1. Evaluation of ACL Reconstruction Techniques.

Knees will be prepared as described above. Intact and deficient ACL data will be obtained as described above. Knees will then be randomized into three groups: TT ACL reconstruction, AM ACL reconstruction, and DB ACL reconstruction. The reconstructions will be performed by a sports medicine surgeon who is comfortable with all three techniques. The TT and AM reconstructions will be performed as described in the literature and the DB reconstruction will be performed with the bundles placed in the anatomic positions after transaction. All reconstructions will be with hamstring autografts from the same specimen. Each single bundle reconstruction will be sized to an 8-mm graft, and for the double bundle graft, the individual bundles will be split into AM and PL bundles for a total graft size of 8-mm. Both the tibial and femoral sides will be fixed with aperture fixation and interference screws, and backed up with tibial and femoral posts to decrease the effects of graft loosening between tests. Testing will be performed in triplicate. To confirm the stability of the knee, static AP and IR data will be obtained at different flexion angles as described in a previous study by our group.

2. Data and Power Analysis.

Kinematic data will be collected and reported as described above. Comparisons will be made between each reconstruction group (TT, AM, DB) and statistical analysis will be performed as described above. The logistic regression model described above will be applied to the data collected for each test, and the percent probability of injury will be calculated to judge the knee stability index for each reconstruction technique and compare it to the intact knee state.

A 95% confidence interval is assumed around sensitivity and specificity in order to predict the desired sample size. An AUC of 0.95 is targeted, with a precision of ±0.05, and eight knees tested in each configuration will be required, for a total of 24 knees.

3. Expected Results.

It is anticipated that the AM portal and double bundle technique will better restore overall knee kinematics as measured by our primary variables ($IR_{max}$, $AD_{max}$, and PTV) compared to the TT techniques. In addition, it is predicted that the AM portal and DB techniques will result in a knee stability indices approaching that of an intact knee state, while the TT technique will not.

It is possible that there will be no significant difference noted in the primary variables when comparing the different reconstruction techniques, which may be due to the fact they are equivalent in restoring rotational stability. If this occurs, the secondary variables as described in Section B.5 will be evaluated to confirm the results.

The foregoing description of the embodiments of the invention has been presented for the purpose of illustration; it is not intended to be exhaustive or to limit the invention to the precise forms disclosed. The disclosure above focuses primarily on the knee and on the ACL. However, the method and apparatus are in no way limited to the particular parts of the body, but instead can be used in association with a variety of parts of the body, including various different joints and ligaments, and the method and apparatus can be used to mimic manual tests other than the pivot shift test. Thus, the examples above are provided for illustration of some embodiments of the method and apparatus. Persons skilled in the relevant art can appreciate that many modifications and variations are possible in light of the above disclosure. Accordingly, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon or claiming priority to this application. Each of the references presented below are incorporated by reference herein in their entireties for all purposes.

We claim:

1. An apparatus for performing a mechanical pivot shift test on a knee of a leg, the apparatus comprising:
 a first rigid frame positioned against a first portion of the leg for holding the apparatus against the leg;
 a second rigid frame positioned against a second portion of the leg for holding the apparatus against the leg;
 at least one stabilizer attached to the first rigid frame for stabilizing a portion of the apparatus against a portion of the leg;
 at least one fastening strap positioned around the leg and connecting the first rigid frame and the at least one stabilizer for fastening the apparatus to the leg;
 a first positioning device attached to the first rigid frame and a second positioning device attached to the second rigid frame;
 a tension-applying spring attached to and positioned between the two positioning devices, the tension-applying spring positioned in a specific location and orientation with respect to the knee by the positioning devices, to generate forces and moments about the knee over a range of motion for performance of the mechanical pivot shift test on the knee, wherein at least one of the forces and moments is a valgus torque on the knee, and wherein the mechanical pivot shift test evaluates the knee based on kinematic response of the knee to the generated forces and moments; and
 at least two sensors configured to record the translational and rotational positions of a tibia and a femur of the leg over the range of motion, the recorded translational and rotational positions of the tibia and femur of the leg over the range of motion being used for calculating a stiffness matrix for the knee, the stiffness matrix describing displacements and rotations of the knee in response to the forces and moments applied to the knee.

2. The apparatus of claim 1, wherein the tension-applying spring is a constant-tension spring, wherein one end of the spring is mounted to the first positioning device attached to the first rigid frame and the other end of the spring is mounted to the second positioning device attached to the second rigid frame.

3. The apparatus of claim 1, wherein the positioning devices further comprise rigid spring-positioning rods attached to either end of the spring.

4. The apparatus of claim 3, wherein the positioning devices further comprise rod-positioning hubs that are attached to the spring positioning devices and are moveably attached to at least one of the rigid frames, the rod-positioning hubs being rotating hubs that have at least one preset configuration for a position of the spring-positioning rods.

5. The apparatus of claim 1, wherein the first rigid frame further comprises a femoral rigid frame that holds an upper portion of the apparatus against a thigh of the leg and the second rigid frame further comprises a tibial rigid frame that holds a lower portion of the apparatus against a shin of the leg.

6. The apparatus of claim 1, wherein the at least one stabilizer further comprises a femoral epicondyle stabilizer that is configured to stabilize an upper portion of the apparatus on a bony femoral epicondyle and tibial rigid stabilizer that is configured to stabilize a lower portion of the apparatus on a bony tibial ridge.

7. An apparatus for performing a mechanical pivot shift test on a knee of a leg, the apparatus comprising:
 a fixation system in contact with at least a portion of the leg for mounting the apparatus to the leg and stabilizing the apparatus against the leg;
 a force-applying device attached to the fixation system for generating forces and moments about the knee over a range of motion of the knee for performance of the mechanical pivot shift test of the knee, wherein at least one of the forces and moments is a valgus torque on the knee, and wherein the mechanical pivot shift test evaluates the knee based on kinematic response of the knee to the generated forces and moments;
 at least two sensors associated with the fixation system that are configured to record the translational and rotational positions of a tibia and a femur in the leg over the range of motion; and
 a computer processor, communicatively connected to the at least two sensors, configured to calculate a knee stability index based on the recorded translational and rotational positions of the tibia and the femur in the leg, the knee stability index describing the stability of the knee in response to the forces and moments applied to the knee.

8. The apparatus of claim 7, wherein the force-applying device is a constant-tension spring, wherein one end of the spring is mounted to a first positioning device located at the upper leg and the other end of the spring is mounted to a second positioning device located at the lower leg.

9. The apparatus of claim 7, further comprising a pre-determined signature usable to determine if a medical condition is indicated by the recorded positions of the knee and by the forces and moment generated over the range of motion.

10. The apparatus of claim 7, wherein the knee stability index describes the stability of the knee in response to the forces and moments applied to the knee by a plurality of joint stability parameters.

11. The apparatus of claim 7, wherein the sensors comprise one or more strobing markers that are attached to the leg for transmitting information about positions of the leg to the computer processor.

12. The apparatus of claim 9, wherein the pre-determined signature indicates rotational stability of the knee.

13. The apparatus of claim 7, wherein the apparatus is a mechanical pivot shift apparatus that provides repeatable application of specific multiplanar forces and moments to the knee and measures kinematic response of the knee to the applied forces and moments.

14. The apparatus of claim 7, wherein the computer processor is further configured to allow calculation of a stiffness matrix for the knee based on recorded translational and rotational positions of a tibia and a femur in the leg over the range of motion, the stiffness matrix describing displacements and rotations of the knee in response to the forces and moments applied to the knee.

15. The apparatus of claim 10, wherein the plurality of the joint stability parameters comprise:
   maximum internal tibial rotation;
   maximum anterior displacement; and
   posterior tibial velocity.

16. The apparatus of claim 1, wherein the stiffness matrix describes the displacements and rotations of the knee in response to the forces and moments applied to the knee by a plurality of knee stiffness parameters and the plurality of the knee stiffness parameters comprise:
   initial internal rotation;
   initial anterior displacement;
   lateral compartment displacement; and
   medial compartment displacement.

17. The apparatus of claim 1, wherein the recorded translational and rotational positions of the tibia and the femur in the leg are used for calculating a knee stability index, the knee stability index describing the stability of the knee in response to the forces and moments applied to the knee.

18. The apparatus of claim 1, further comprising a signal evaluator configured to:
   determine significant differences between at least one of a plurality of primary joint configuration parameters associated with the stiffness matrix and a corresponding reference configuration parameter associated with a pre-determined signature indicative of a particular knee defect; and
   evaluate performance of the mechanical pivot shift test on the knee based on the determined significant differences.

19. The apparatus of claim 1 wherein the two positioning devices position the tension-applying spring with a pre-defined distance from the leg.

20. The apparatus of claim 1 wherein the valgus torque on the knee is inward and designed to sublux the tibia on the femur on the knee in an anterior cruciate ligament (ACL)-deficient state.

21. The apparatus of claim 7, further comprising a signal evaluator configured to:
   determine significant differences between at least one of a plurality of primary joint configuration parameters associated with the stiffness matrix and a corresponding reference configuration parameter associated with a pre-determined signature indicative of a particular knee defect; and
   evaluate performance of the mechanical pivot shift test on the knee based on the determined significant differences.

22. The apparatus of claim 7, wherein the valgus torque on the knee is inward and designed to sublux the tibia on the femur on the knee in an anterior cruciate ligament (ACL)-deficient state.

* * * * *